United States Patent [19]

Narang et al.

[11] Patent Number: 4,792,602

[45] Date of Patent: Dec. 20, 1988

[54] ADAPTORS, AND SYNTHESIS AND CLONING OF PROINSULIN GENES

[75] Inventors: Saran A. Narang, Ottawa, Canada; Ray J. Wu, Ithaca, N.Y.

[73] Assignee: Cornell Research Foundation, Inc., Ithaca, N.Y.

[21] Appl. No.: 562,045

[22] Filed: Dec. 16, 1983

Related U.S. Application Data

[63] Continuation of Ser. No. 275,161, Jun. 19, 1981.

[51] Int. Cl.$^4$ .................. C07H 5/12; C12N 15/00
[52] U.S. Cl. ........................................ 536/27; 435/68; 435/172.3; 935/6; 935/13; 935/23
[58] Field of Search ............... 435/68, 172.3; 935/13, 935/23, 6; 536/27

[56] References Cited

U.S. PATENT DOCUMENTS

| | | | |
|---|---|---|---|
| 4,237,224 | 12/1980 | Cohen et al. | 435/68 |
| 4,321,365 | 3/1982 | Wu et al. | 435/68 |
| 4,431,740 | 12/1984 | Bell et al. | 435/13 |

FOREIGN PATENT DOCUMENTS 7900399 6/1979 PCT Int'l Appl. .

OTHER PUBLICATIONS

Villa-Komaroff et al, A Bacterial clone synthesizing Pro-Insulin, *Proc. Natl. Acad. Sci. U.S.A.* vol. 75, 1978, pp. 3727–3731.
Roberts, Directory of Restriction Endonucleases, *Methods in Enzymology* vol. 68, 1979, pp. 27–41.
Rothstein et al., Synthetic Adaptors for Cloning DNA, *Methods in Enzymology*, vol. 68, 1978, pp. 98–109.
Brevet et al., Promotion of Insertions and Deletions by Translocating Segments of DNA Carrying Antibiotic Resistance Genes, in *DNA Insertion Elements, Plasmids and Episomes*, 1977, Cold Spring Harbor Labs.
Marians et al., *Nature*, 263: 744–748 (1976).
Heyneker et al., *Nature*, 263: 748–752 (1976).
Scheller et al., *Science*, 196: 177–180 (1977).
Bahl et al., *Gene*, 1:81–92 (1976).
Pribnow, *Proc. Nat. Acad. Sci.*, 72: 784–788 (1975).
Polisky et al., *Proc. Nat. Acad. Sci.*, 73: 3900–3905 (1976).
Itakura et al., *Science*, 198: 1056, 1066 (1977).
Goeddel et al., *Nature*, 281: 544–548 (1979).
Goeddel et al., *Proc. Nat. Acad. Sci.*, :106–110 (1979).
Ullrich et al., Proceedings of the Symposium on Proinsulin, Insulin and C-Peptide, Tokushima, 12–14 Jul., 1978, pp. 20–26 (1976).
Crea et al., *Proc. Nat. Acad. Sci.*, 75: 5765 (1978).
Vella-Konaroff et al, *Proc. Nat. Acad. Sci.*, 75:3727 (1978).

*Primary Examiner*—Christine M. Nucker
*Attorney, Agent, or Firm*—Jones, Tullar & Cooper

[57] ABSTRACT

A human-like proinsulin gene and its analogs, have been synthesized by a combination of chemical and enzymatic methods. A number of different human-like proinsulin gene analogs with altered C-chains have also been designed and can be readily constructed as described. As a part of the strategy, an adaptor for trimming DNA has been designed, synthesized and used to recover the A-chain insulin gene with the desired sequence from a hybrid plasmid; a related adaptor for trimming DNA has been designed to shorten the C-chain gene or any gene. The synthetic proinsulin gene has been joined to a replicable cloning vehicle and the hybrid DNA transferred to a host cell. The transformed host cell has been shown to contain the desired human-like proinsulin gene.

6 Claims, No Drawings

ADAPTORS, AND SYNTHESIS AND CLONING OF PROINSULIN GENES

This application is a continuation of application Ser. No. 275,161, filed June 19, 1981.

FIELD OF THE INVENTION

This invention is concerned with the synthesis of exact DNA genetic sequences and the joining of the synthetic gene to replicable cloning vehicles. Of particular concern is the total synthesis of the human-like proinsulin gene, the insertion of the gene into cloning vehicles, and the transferring of the hybrid DNA molecules into host cells, the transformed cells thus having the ability to produce the specified human-like proinsulin protein. In this application, several adaptors for trimming DNA have been described, and they can trim any DNA down to a desired length.

BACKGROUND AND PRIOR ART

In recent years, methods have been developed (see "Molecular Cloning of Recombinant DNA", eds., W. A. Scott and R. Werner, Academic Press Inc., 1977), (1) for the in vitro joining by DNA ligase of a DNA segment to be cloned (scheme 1, structure I) to a cloning vehicle (DNA capable of independent replication, structure II), (2) for introducing the hybrid DNA molecule (recombinant DNA, structure III) into a suitable host cell, (3) for selecting and identifying the transformed cells carrying the desired hybrid DNA (cloned DNA as a hybrid DNA, structure IV), (4) for amplifying the desired cloned DNA in the transformed cells, and (5) for expressing the cloned DNA as a protein product. In most reported cases, the DNA molecules isolated from cells or viruses have been fragmented by restriction enzyme digestion or by physical shearing or by reverse transcription copy of messenger to cDNA before cloning.

Scheme I
The cloning of a DNA fragment in a bacterium

The triangles at the ends of DNA molecules represent the proper sequence that allows matching and ligation of the ends with other DNA molecules.

(I) DNA to be cloned  (II) Cloning vehicle

-continued
Scheme I
The cloning of a DNA fragment in a bacterium

The triangles at the ends of DNA molecules represent the proper sequence that allows matching and ligation of the ends with other DNA molecules.

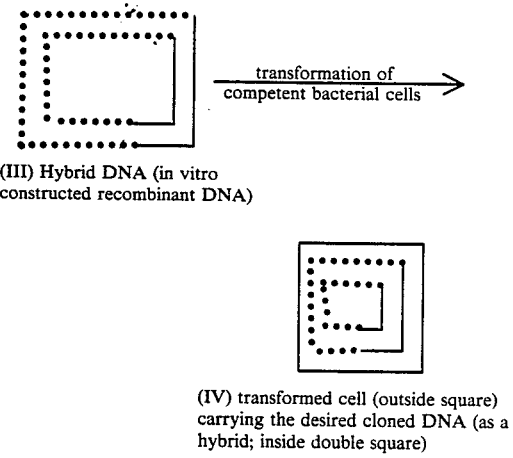

(III) Hybrid DNA (in vitro constructed recombinant DNA)

(IV) transformed cell (outside square) carrying the desired cloned DNA (as a hybrid; inside double square)

Protein synthesis in bacteria using a segment of transferred DNA derived from mouse as the blue print was shown by Chang et al. (Cell 6, 231–244, 1975). Still other examples of the cloning of natural foreign DNA have been described recently (Goeddel et al, Nature 281, 544–548, 1979; etc.).

Methods for the total chemical synthesis of oligodeoxynucleotides of up to 20-nucleotides-long have been well established by using either the phosphodiester method (H. G. Khorana, J. Mol. Biol. 72, 209, 1972) or the improved phosphotriester method (H. M. Hsiung and S. A. Narang, Nucleic Acids Res. 6, 1371, 1979; S. A. Narang et al, Methods in Enzymology, Vol. 65, 610, 1980, and Vol. 68, 90, 1979). The latter method is now the preferred method because of its higher speed, better yield and purity of products, and has been used to prepare defined DNA sequences of longer length.

A few chemically-synthesized DNA sequences, such as the lactose operator (Marians, Wu, et al, Nature 263, 744, 1976) and the tyrosine tRNA gene (Khorana, Science 203, 614, 1979), have been successfully cloned in E. coli and the expression of the cloned DNA detected in subsequent cultures. Recent reports have indicated that human brain hormone somatostatin (Itakura et al, Science 198, 1056, 1977) and human growth hormone (Goeddel et al, Nature 281, 544, 1979) have been produced in a transformed bacterial host which had the transferred synthesized gene.

In the pancreas of animals, preproinsulin (S. J. Chan and D. F. Steiner, Proc. Nat. Acad. Sci. 73, 1964, 1976) is synthesized as the precursor of insulin. The general structure of proinsulin is $NH_2$-B chain-(C chain)-A chain-COOH; it is converted to insulin by the action of peptidases in the pancreatic islet tissue which remove the C-chain by cleavage at the positions of the two arrows shown in Formula 1 for the human proinsulin (Oyer et al, J. Biol. Chem., 246, 1375, 1971). The B-chain and A-chain of insulin are held together by two disulfide cross-linkages which are formed at the correct location at the stage of the proinsulin.

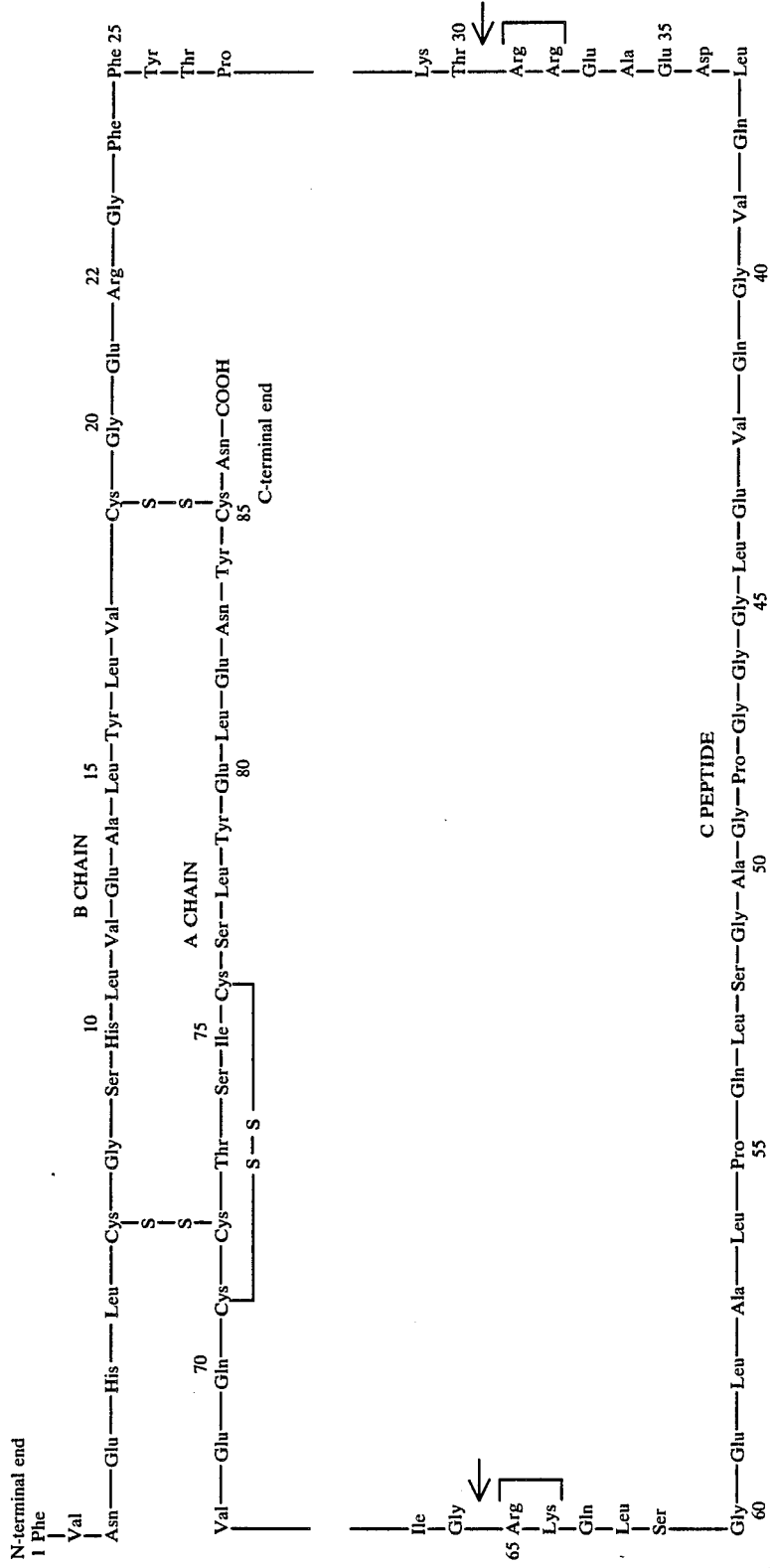
Formula I
THE STRUCTURE OF HUMAN PROINSULIN. B chain, amino acids 1–30, C peptide, amino acids 31–65; A chain, amino acids 66–86. Residues 31, 32, 64, 65 will be excised during processing.

Using a biological method, Ullrich et al, (Science 196, 1313, 1977) and Villa-Komoroff et al, (Proc. Nat. Acad. Sci. 75, 3727, 1978) succeeded in cloning the coding region of rat proinsulin I. Using a chemical method, Crea et al, (Proc. Nat. Acad. Sci. 75, 5765, 1978), synthesized, and Goeddel et al (Proc. Nat. Acad. Sci. 76, 106, 1979), cloned, an insulin A-chain gene and a B-chain gene, separately. The codons selected for these synthetic genes were arbitrary and quite different from the natural human DNA sequence. On culturing, the bacteria produced an insulin A-chain protein and B-chain protein which were separately treated to remove the extraneous $\beta$-galactosidase and methionine.

In U.S. patent application Ser. No. 843,422, filed Oct. 19, 1977, by R. Wu et al, and U.S. patent application Ser. No. 129,880, filed Mar. 27, 1980, by S. A. Narang et al, synthetic adaptor molecules were described for attachment to the ends of DNA sequences, such as synthetic insulin A-chain and B-chain gene, for joining to cloning vehicles or other DNA. These adaptors comprised DNA (oligonucleotide) sequences having particular nucleotide segmnts which are recognition sites for restriction endonucleases and codon triplets. These adaptors can also be used to provide an enzyme recognition site on a duplex DNA sequence or to change from one type of site to another.

SUMMARY OF THE INVENTION

This invention includes retrieving (trimming) adaptor oligodeoxynucleotides useful for retrieving (and trimming) genes from replicable DNA, comprising: (a) a recognition site for restriction endonucleases of the type Hph I and Mbo II; and (b) from 1 to 7 additional nucleotides downstream of the recognition site. These adaptors may be non-symmetrical or symmetrical. Also included are symmetrical trimming adaptor oligodeoxynucleotides having the formula selected from

where X and Y are any complementary nucleotides and n is selected from 0–7. These adaptors can be used for trimming away (removing) up to 8 base pairs from the end of a DNA molecule, by steps comprising: (a) blunt end ligating to said DNA end a trimming adaptor where the number of additional nucleotides is chosen to give the desired digestion cleavage location, (b) digesting the resulting adapted DNA with the endonuclease whose recognition site is present in the adapter, to cleave the 5' strand at the desired location downstream of said recognition site, (c) where undesired nucleotide base remains in the 3' strand, digesting the remaining DNA with an enzyme of the type DNA polymerases and exonucleases including Aspergillus S1 nuclease and $E.$ $coli$ polymerase I to leave the end of the DNA blunt or flush, and (d) recovering the DNA free of the undesired base pairs.

A novel codon sequence for insulin C-chain gene (DNA) has been provided. Shorter or mini-C-chains have also been developed, and used to form analogs of proinsulin. A restriction enzyme recognition site was incorporated in these C-chains by selection of appropriate codons at a selected location to facilitate opening and insertion of a DNA information sequence.

The invention includes combining selected A-, B- and C-chains into novel proinsulin genes, ligating these genes to replicable cloning vehicles and transferring the resulting hybrid into host cells. In particular, for example, a synthetic human-like proinsulin gene (formula 2) has been synthesized by a combination of chemical and enzymatic methods. A start signal (ATG) and an EcoRI cohesive and (5' AATT) was placed at the 5' end (left-hand end) of the gene, and a stop signal (TGA) and a BamHI cohesive end (5' GATC) was placed at the 3' end of the gene. This adapted proinsulin gene was joined to a replicable cloning vehicle that can enter a cell and replicate itself together with the cloning vehicle. The transformed host cell progeny was shown by DNA sequence analysis to contain the exact input proinsulin gene. A plasmid cloning vehicle has been constructed which includes a lactose promoter and produces several hundred copies of the proinsulin gene per cell.

Formula 2

DNA SEQUENCE OF HUMAN-LIKE PROINSULIN GENE. The duplex structure represented by base pairs 1 through 258 constitutes the proinsulin gene. The B-chain, C-chain and A-chain start from base pairs 1, 91 and 196, respectively.

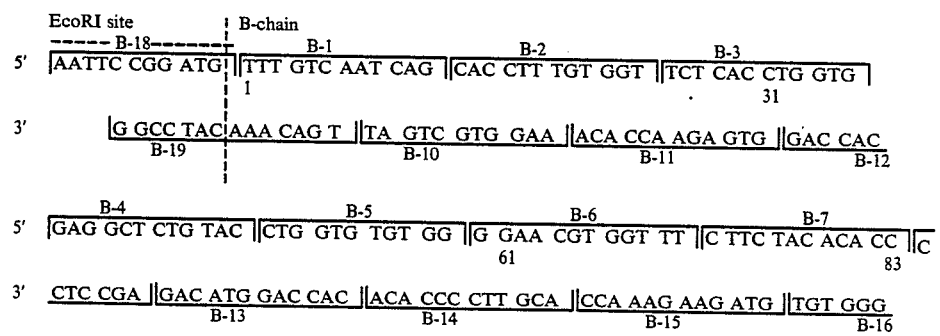

-continued

Formula 2
DNA SEQUENCE OF HUMAN-LIKE PROINSULIN GENE. The duplex structure represented by base pairs 1 through 258 constitutes the proinsulin gene. The B-chain, C-chain and A-chain start from base pairs 1, 91 and 196, respectively.

```
                  |C-chain
        B-8       |   C-1          C-2              C-3
5'  AAG ACC|CGT CGT |GAA GCT GAA GAC |CTT CAA GTG GGT |CAA GTT GAA CTT |
           |91                                  121

3'  TTC TGG |GCA GCA CTT CGA |CTT CTG GAA GTT CA |C CCA GTT CAA |CTT GAA
              C-9                C-10                 C-11        C-12

C-4            C-5              C-6              C-7
5'  |GGT GGG GGT |CCT GGT GCG GGT |TCT CTT CAA CCT |TTG GCT CTC GAG G |GA

3'  CCA CC |C CCA GGA CCA CG |C CCA AGA GAA |GTT GGA AAC CGA |GAG CTC CCT
              C-13              C-14           C-15              C-16

|A-chain
           C-8              |
5'  TCA CTT CAA AAG CGT | GGC ATT GTG GAG CAG TGC TGC ACC AGC ATC TGC
    181                 | 196

3'  AG |T GAA GTT TTC GCA | CCG TAA CAC CTC GTC ACG ACG TGG TCG TAG ACG
        C-17              |

5'  TCC CTC TAC CAA CTG GAG AAC TAC TGC AAC TGA G        3'
                241                         258

3'  AGG GAG ATG GTT GAC CTC TTG ATG ACG TTG ACT CCTAG    5'
                                                 BamHI site
```

DETAILED DESCRIPTION AND PREFERRED EMBODIMENTS

A. The Adaptors for Trimming DNA

The principle behind this type of retrieving (trimming) adaptor is based on the knowledge that certain restriction endonucleases such as HphI and MboII cleave DNA eight nucleotides away from their recognition sequence (R. J. Roberts, Methods in Enzymol. 68, 27, 1980). In formula 3, the five nucleotides with a line drawn above constitute the recognition sequence, where N stands for any nucleotide.

Formula 3
Recognition sequence and mode of cleavage of HphI and MboII (a)
```
HphI   5'  GGTGANNNNNNNN ↓
       3'  CCACTNNNNNNN  ↑
```

(b)
```
MboII  5'  GAAGANNNNNNNN ↓
       3'  CTTCTNNNNNNN  ↑
```

We have designed and synthesized adaptors for trimming DNA as symmetric adaptors (non-symmetric adaptors based on formula 3 can also be used);

Formula 4
HphI and MboII adaptors for trimming DNA (a-1)
```
HphI   5'  TCACCGGTGA
       3'  AGTGGCCACT
```

(b-1)
```
MboII  5'  TCTTCGAAGA
       3'  AGAAGCTTCT
```

This type of adaptor for trimming DNA can be blunt-end ligated to any DNA from which 8 nucleotides at the end can be removed. MboII adaptor is used as an example to remove eight nucleotides N N N N N N N N from the end of a cloned insulin A-chain gene.

Formula 5
Scheme for removing 8 base pairs from any DNA molecule using MboII retrieving adaptor

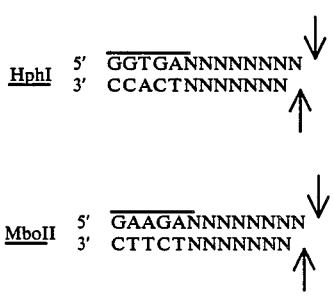

```
                       1        8
5' T C T T C GAAGA    N N N N N N N N  cloned        (b-2)
                   +                   A-chain
3' AGAAGC T T C T    N N N N N N N N   gene
``` blunt-end ligation
(T4 DNA ligase)
↓
```
                          1        8
5' T C T T C GAAGA N N N N N N N N  cloned
3' AGAAGC T T C T N N N N N N N N   A-chain gene
```

↓ MboII endonuclease

-continued
Formula 5
Scheme for removing 8 base pairs from any DNA molecule
using MboII retrieving adaptor

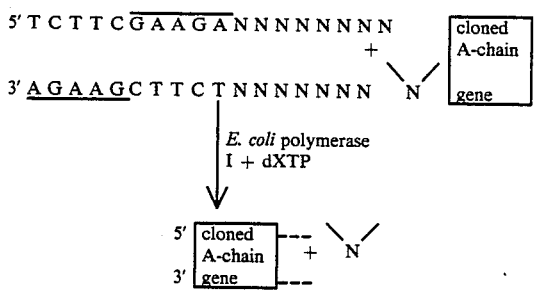

the dXTP is chosen so that it is identical to the one adjacent to N at the 3' end of the cloned A-chain gene, e.g. if the nucleotide "X" is C then dCTP is used.

In principle, adaptors for trimming DNA of this type containing 1 to 7 additional nucleotides beyond the MboII or HphI recognition sites can be used to rim off 7 to 1 base pairs from the ends of any DNA duplex (Narang et al, Nucleic Acids Res. Symposium Series No. 7, 377, 1980).

B. Chemical synthesis of deoxyribooligonucleotide fragments constituting the sequence of human proinsulin gene The chemical synthesis of all the deoxyribooligonucleotides constituting the sequence of human proinsulin DNA as in formula 2 and various adaptors were achieved by the modified phosphotriester approach developed in one of our labs in 1973 (Can. J. Chem. 51, 3649, 1973; S. Narang et al, Methods of Enzymology 65, 610, 1980; and S. Narang et al, Methods in Enzymology 68, 90, 1979). The main features of our approach are:

(i) use of 5'-dimethoxytrityl-deoxytribomononucleoside 3'-phosphotriester (monomer) as a starting material;

(ii) condensation between 5'-dimethoxytrityl-deoxyribomononucleoside 3'-phosphodiester with a 5'-hydroxy containing component to yield a dinucleotide containing an internucleotidic phosphotriester linkage as a neutral species which is amenable to all the conventional techniques of organic chemistry for their isolation; and (iii) formation of the desired product in a higher yield because of the absence of side products.

The synthesis of all the deoxyribooligomers (10–20 units length) were constructed from the sixteen possible dimer blocks. Each coupling reaction was performed using almost stoichiometric amounts of each component in the presence of mesitylenesulfonyl tetrazole, as coupling reagent (S. Narang et al, U.S. Pat. No. 4,059,592, 22 Nov. 1977), for 30–45 min. at room temperature. After work-up, the desired product was isolated by the reversed-phased chromatographic technique developed by H. M. Hsiung et al, Nucleic Acid Res. 6, 1371, 1979. After the completion of synthesis, the 5'-dimethoxytrityl group was removed using 2% benzenesulfonic solution in chloroform-methanol (J. Stawinski et al, Nucleic Acid Res. 4, 353, 1977). All the other protecting groups were removed by two-step concentrated ammonia treatments (H. M. Hsiung et al, Nucleic Acid Res. 8, 5753, 1980). Each of the unprotected oligomers was purified on PEI-tlc plate and sequenced by the mobility-shift method (C. D. Tu et al, Anal. Biochem. 74, 73, 1976). Each fragment sequence was confirmed and their autoradiographs have been published (Nucleic Acid Res. 6, 1371, 1979; 7, 2199, 1979; 8, 5753, 1980).

C. Synthesis and Cloning of the Proinsulin Gene

The human-like proinsulin gene is given in formula 2. This codon sequence (base pairs 1 through 258) was selected by us and codes for the human-like proinsulin, the structure of which is shown in formula 1. The coding sequence (gene sequence) was based on that of the rat proinsulin gene (Ullrich et al, Science 196, 1313, 1977) wherever the amino acids are in common. The amino acids in positions 3, 9, 30, 34, 37, 40, 42, 49, 52, 53, 60, 61, 62 and 69 for the human proinsulin are different than those in rat, thus in these positions a coding sequence for the human proinsulin was selected. In formula 2, the nucleotides 1–90, 91–195 and 196–258 code for human-like insulin chain B, chain C and chain A, respectively. The codons we selected form a unique combination.

The human-like proinsulin gene was assembled in the following way. The gene coding for the B-chain and a major portion of the C-chain was constructed as one unit which included the start signal (on fragments B-18 and B-19) and the coding sequence (nucleotides 1–178 of the upper strand and 1–182 of the lower strand of formula 2). This synthetic DNA was constructed from 32 synthetic fragments of 10 to 13 nucleotides in length. Four to six fragments were first joined together by cohesive-end ligation using DNA ligase to give six groups of fragments (a–f in formula 6). The sequence of each fragment was shown in formula 2.

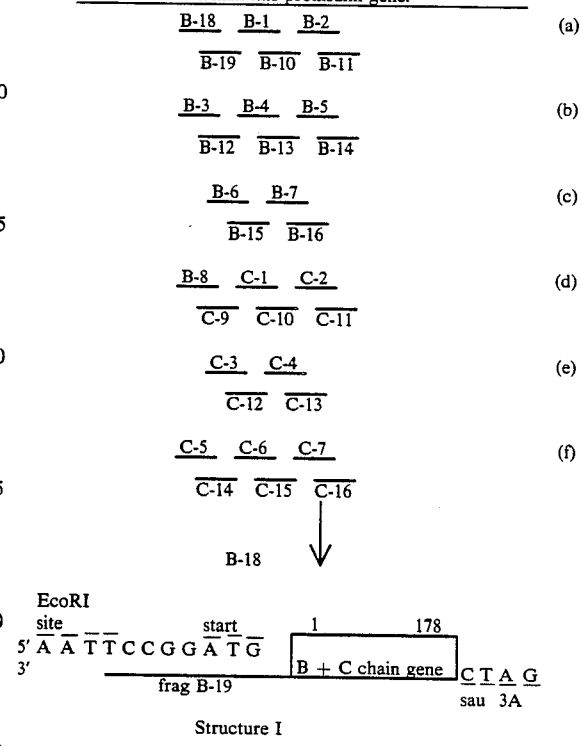

In constructing each group of fragments, about 800 pmoles of each synthetic fragment (4 to 6 fragments) was phosphorylated at its 5'-end with $^{32}P$ using polynucleotide kinase. THe phosphorylated fragment was purified on a 20% polyacrylamide gel. About 500 pmoles of each purified fragment was annealed in 30 μl volume at 65° C. and slowly cooled to 0° C. Concentrated DNA ligase buffer was added to give the following final concentrations: 50 mM Tris-HCl (pH 7.6), 10 mM MgCl$_2$, 10 mM dithiothreitol, 100 μM ATP. T$_4$ polynucleotide ligase (0.4 unit) was added and the mixture incubated at 12° C. for 24–36 hours. The ligation product was purified on a 15% polyacrylamide gel (denaturing condition). The yield of fragments incorporated into each group (a through f) varied between 120 and 250 pmoles.

In the next step, one group was joined to the adjacent group (e.g. group a to b) by cohesive-end ligation until all six groups were connected to give structure I of formula 6. The ligation conditions are the same as given in the paragraph above. The yield of structure I was about 20 pmoles.

The cloned human-like insulin A-chain gene has been reported in a pending U.S. patent application Ser. No. 129,880, filed Mar. 27, 1980, by S. A. Narang and R. J. Wu, which is hereby incorporated by reference. The insulin A-chain gene has been retrieved (recovered) from the clone by digestion with EcoRI restriction enzyme, which exposed the EcoRI site eight nucleotides away from the A-chain gene as shown in formula 7.

The blunt-end ligation was carried out in 15 l of a reaction mixture containing 50 mM Tris-HCl (pH 7.6), 10 mM MgCl$_2$, 10 mM dithiothreitol 100 μM ATP, 100 pmoles of the self-complementary MboII adaptor, 30 pmoles of cloned A-chain gene, and 0.3 units of T$_4$ polynucleotide kinase. Incubation was at 12° C. for 40 hours.

Cleavage of DNA shown in formula 8 with MboII restriction enzyme (which cleaves DNA at the arrows, eight nucleotides away from recognition sequence GAAGA), followed by E. coli polymerase I (in the presence of $^{32}$P dCTP or cold dCTP to insure that the end of DNA is flushed), results in the removal of the eight extra base pairs from the A-chain gene. The retrieved A-chain gene was next cleaved with BamHI restriction enzyme, which gave the following structure:

Formula 9
Retrieved Insulin A-chain Gene.

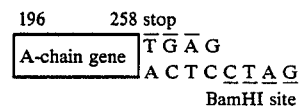

BamHI site

The retrieved insulin A-chain gene was blunt-end ligated to segments C-8 and C-17 to give structure II.

Formula 7
The Cloned Insulin A-chain Gene.

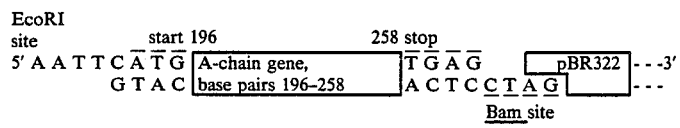

Note that the 3' end (right-hand end) of the cloned A-chain gene at this stage is still joined to the stop adaptor and pBR322 plasmid cloning vehicle. The eight extra nucleotides at the 5' end (left-hand side) of the insulin A-chain gene (which includes the start signal) has been removed by using a MboII trimming adaptor. The DNA in formula 7 was first repaired by using dATP and dTTP in the presence of AMV reverse transcriptase. A decanucleotide MboII adaptor for trimming DNA was next blunt-end ligated to the repaired end to give:

Structure II

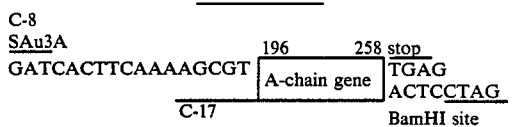

Structure II was then joined to structure I at their Sau3A sites by cohesive-end ligation under the same conditions as given above for each group of fragments, to give the proinsulin (B+C+A chain) gene as shown in formula 10, lower part.

Formula 8
MboII Adaptor Ligated to the Repaired Cloned A-chain Gene

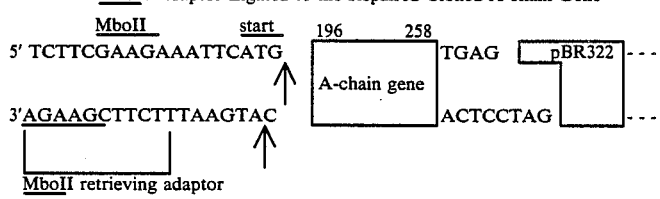

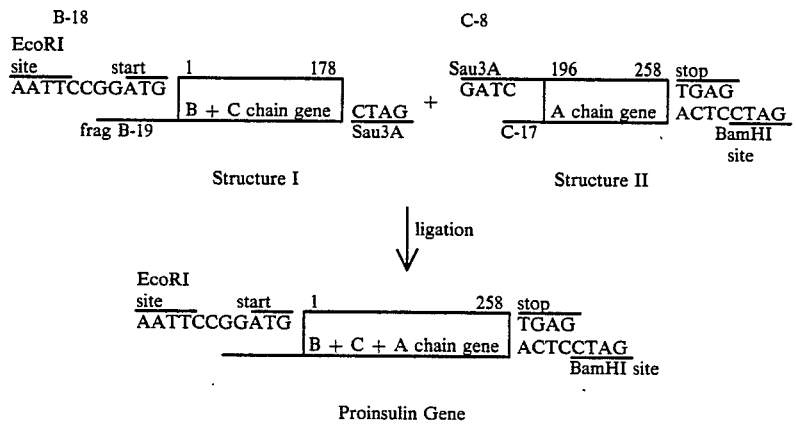

Formula 10
Scheme for the construction of a human-like proinsulin gene from synthetic fragments It must be pointed out that the human-like proinsulin gene can also be constructed by joining the same 32 fragments of the B+C chain and the retrieved A-chain gene in several different ways.

The natural human proinsulin contains a C-chain consisting of 35 amino acids. The efficiency of removing the C-chain by peptidases to produce biologically active insulin (B+A chains) may be influenced by the length of the C-chain. Thus, we designed several methods to product proinsulin analogs by changing the length of the C-chain gene, which would lead to proinsulin analogs with different lengths of the C-chain. One or several of the proinsulin analogs may prove to be superior than the natural proinsulin in giving a higher yield of the biologically active insulin, and possibly the modified C-chains will have less physiological side effects.

(a) In one method, the length of the C-chain gene (normally 35 amino acids X3=105 base pairs) can be assembled by omitting two or more fragments to give only 93, 84 or 72 base pairs, respectively. This can be accomplished by constructing the B+C chain in a similar way as that in formula 6 except that groups d, e, f have been redesigned (see formula 11) by eliminating fragments C-5 and C-13 to give a C-chain shorter by 12 base pairs (see formula 11). In a similar manner, the elimination of fragments C-3, C-4, C-11, and C-12, gave a C-chain shorter by 21 base pairs, or the elimination of fragments C-3, C-4, C-5, C-11, C-12, and C-13, gave a C-chain shorter by 33 base pairs.

Formula 11
Scheme for the construction of a shorter B + C chain of a human-like proinsulin gene. Groups (a), (b) and (c) are the same as in formula 6 and are not shown.

(d) B-8   C-1   C-2
    ―――   ―――   ―――GGGT
    C-9   C-10

(e) CCCA―C-3―  ―C-4―
        ―――   ―――GGGT
        C-11   C-12

Formula 11
Scheme for the construction of a shorter B + C chain of a human-like proinsulin gene. Groups (a), (b) and (c) are the same as in formula 6 and are not shown.

(f) CCCA―C-6―  ―C-7―
        ―――   ―――   ―――
        C-14   C-15   C-16

These constructions are possible since the nucleotide sequence at the junctions of the eliminated fragments (C-2, C-4, and C-5) are identical and they all contain a 3' protruding sequence d(G-G-G-T) in the upper strand (see formula 2, underlined nucleotides, and formula 11). Thus, we can eliminate one or two of three segments from the upper strand and still allow annealing with the d(C-C-C-A) sequence in the lower strand to give C-chains of different length. Once the different shortened C-chains are assembled, each will be joined to groups (a), (b), and (c) of formula 6 to give shortened B+C chain gene similar to structure I of formula 10. Finally, shortened structure I is jointed to structure II of formula 10 to give shortened proinsulin genes as analogs of the normal gene.

(b) The C-chain gene can be shortened to only 18 base pairs by ligating the following synthetic fragments between the right-hand end of the B-chain gene and the left-hand end of the A-chain gene as follows:

Formula 12
Mini-C-chain coding sequence of human proinsulin gene

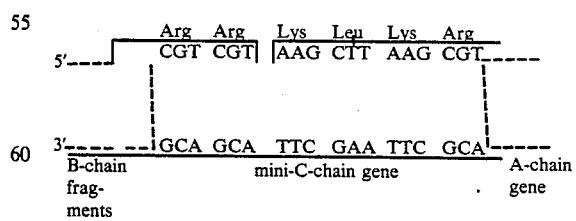

The human-like proinsulin gene (chain B-C-A), or its analogs, which carries a start signal at the 5' end (left-end) and the stop signal at the 3' end (right-end) was jointed to EcoRI- and BamHI-digested pBR322 plasmid and the resulting hybrid DNA used to transform E.

coli (strain 5346). This strain and the containment facilities used conformed to current recombinant DNA regulations. The desired clones were identified by colony hybridization (Grunstein and Hogness, Proc. Nat. Acad. Sci. 72, 3961, 1975) with $^{32}$P-labelled C-chain fragment (17-32 nucleotides long), and $^{32}$P-labelled cloned A-chain fragment. Among the positive clones, the exact sequence of several cloned proinsulin genes was determined by DNA sequence analysis.

The C-chain gene in the cloned human-like proinsulin gene also can be shortened after digesting the latter with Sau3A restriction enzyme to give a DNA structure in which the right-hand end is similar to that shown in Structure I above, and the left-hand end includes all of the B-chain gene and an additional 325 base pairs of the DNA from the cloning vehicle pBR322. This molecule can be shortened from the right-hand end in two ways:

(i) by removing the 4 protruding nucleotides (5′ GATC) by S1 nuclease digestion (Vogt et al, Europ. J. Biochem. 33, 192, 1973) and joining a Mbo II retrieving adaptor by blunt-end ligation. After carrying out the steps shown in Formula 5 above, 8 base pairs can be removed from the right-hand end to shorten this part of the C-chain by 12 base pairs (4+8). By repeating the Mbo II retrieving adaptor procedure (Formula 5) one or more cycles, but using the following adaptor (Formula 13), 6 base pairs can be removed in each cycle from the right-hand end of the already shortened C-chain gene.

Formula 13
A Mbo II retrieving adaptor containing two additional base pairs at each end (N, N′ are any complementary nucleotides)

5′ N N T C T T C G A A G A N′N′

3′ N′N′ A G A A G C T T C T N N

By using the above methods, the C-chain gene of the proinsulin can be shortened by a total of 12, 18, 24 or 30 base pairs leftward from the nucleotide #182 of Formula 2 above.

(ii) by digesting the DNA with a combination of exonuclease III and S1 nuclease (Wu et al, Biochem. 15, 734, 1976; Roberts et al, Proc. Natl. Acad. Sci. 76, 760, 1978) or with BAL31 (Legerski et al, Nucleic Acids Res. 5, 1445, 1978; Talmadge et al, Proc. Natl. Acad. Sci. 77, 3369 and 3988, 1980). In this method from about 6 to 81 base pairs can be removed, and those DNA molecules with a multiple of 3 base pairs removed (e.g. 6, 9, 12, 15, . . . 81) can be selected after cloning and DNA sequence analysis.

The C-chain gene can be lengthened by digesting the cloned human-like proinsulin gene with Sau3A restriction enzyme as described above and inserting DNA fragments of different lengths. For example, the 5′ protruding end (5′ GCTA) can be joined by cohesive-end ligation to another molecule of synthetic fragment C-16 followed by C-7. After repair synthesis with 4 dNTP and the AMV reverse transcriptase, the blunt-ended DNA is now 13 base pairs longer. When this molecule is blunt-end ligated to the S1 nuclease digested structure II above, which digestion removed 4 base pairs from the retrieved and modified insulin A-chain gene, the net result is an addition of 9 base pairs to the C-chain of the proinsulin gene (codes for three additional amino acids). Using the same procedure but adding C-16, C-7, C-15 and C-6 fragments, the end result is the addition of 21 base pairs (seven additional amino acids). Similarly, other multiples of three base pairs can be added.

After the modification of the C-chain gene, which is still attached to the B-chain gene and some pBR322 DNA, it can be blunt-end ligated to the retrieved and modified insulin A-chain gene (Structure II, above) after cleaving off the 4 protruding nucleotides (5′ GATC at the Sau3A site) at the left-hand end by S1 nuclease (as mentioned in the previous paragraph). The product is then digested by EcoRI and BamHI restriction enzymes to release the shortened proinsulin gene (corresponding to the parent structure shown at the bottom of Formula 10, above), and ligated by cohesive-end ligation to EcoRI- and BamHI-digested pBR322 plasmid and cloned as described previously.

For maximum expression, the cloned proinsulin gene can be excised by digestion of the cloned hybrid plasmid DNA with EcoRI and BamHI endonucleases. The BamHI end can be converted to an EcoRI end by using an EcoRI-BamHI conversion adaptor of the type reported in U.S. patent application Ser. No. 129,880, filed Mar. 27, 1980, by S. A. Narang and R. J. Wu. The conversion adaptor has the structure:

Formula 14
EcoRI-BamHI Conversion Adaptor

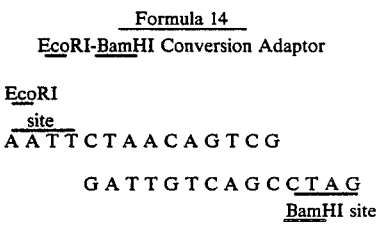

EcoRI
site
5′ A A T T C T A A C A G T C G

3′          G A T T G T C A G C C T A G
                                    BamHI site The resulting adapted proinsulin gene carrying an EcoRI site at each end can be ligated to a plasmid such as pBGP 120 (Polisky et al, Proc. Nat. Acad. Sci. 73, 3900, 1976) or pLL70 (Lau and Wu, unpublished result), adjacent to a strong lactose promoter for expression. This reconstructed hybrid plasmid DNA carrying the proinsulin gene can be used to transform E. coli cells and to direct the synthesis of large amounts of the human proinsulin, which is a natural precursor of biologically active insulin. Alternatively, the cloned proinsulin gene can be joined to the lactose promoter and then to plasmid pKN402 (Uhlin et al, Gene 6, 91, 1979), or a derivative of it, which can produce over 200 copies of the plasmid per E. coli cell. The copy number of this plasmid is at least seven times more than that of pBGP120 or pBR322. Thus, over 200 copies of the proinsulin gene can by synthesized per E. coli cell to yield up to 500,000 copies of the proinsulin protein per cell.

The E. coli proinsulin clone is being maintained in the Dept. of Biochemistry at Cornell University, Ithaca, N.Y. and will be made available as required.

We claim:

1. A synthetic adaptor oligodeoxynucleotide, useful for retrieving and trimming genes from replicable DNA, comprising:
 (a) a recognition site for restriction endonucleases comprising Hph I and Mbo II, and
 (b) from 1 to 7 additional nucleotides downstream of the recognition site,
 said adaptor being ligatable to a preselected DNA molecule and by varying the number of additional nucleotides (b) being adapted to allow controlled trimming of 7 to 1 base pairs from the end of said preselected DNA molecule.

2. The adaptor of claim 1 having the formula

where N and N' are any complementary nucleotides and n is selected from 1 to 7.

3. The adaptor of claim 1 having the formula

where N and N' are any complementary nucleotides and n is selected from 1 to 7.

4. A synthetic symmetrical trimming adaptor oligodeoxynucleotides having the formula selected from:

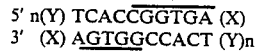

and

where X and Y are any complementary nucleotides and n is selected from 1 to 7, said adaptor being ligatable to a preselected DNA molecule and by varying n being adapted to allow controlled trimming of up to 7 base pairs from the end of said DNA molecule.

5. The adaptor molecule of claim 1 ligated to a DNA information sequence to give an adapted DNA.

6. The adaptor molecule of claim 4 ligated to a DNA information sequence to give an adapted DNA.

* * * * *